US005574075A

United States Patent [19]

Draenert

[11] Patent Number: 5,574,075
[45] Date of Patent: Nov. 12, 1996

[54] MATERIAL AS A STARTING MATERIAL FOR THE PREPARATION OF BONE CEMENT, PROCESS FOR ITS PREPARATION AND PROCESS FOR THE PREPARATION OF BONE CEMENT

[76] Inventor: Klaus Draenert, Gabriel-Max-Str. 3, W-8000 Munchen 90, Germany

[21] Appl. No.: 39,359

[22] PCT Filed: Oct. 21, 1991

[86] PCT No.: PCT/EP91/02000

§ 371 Date: Jun. 8, 1993

§ 102(e) Date: Jun. 8, 1993

[87] PCT Pub. No.: WO92/06717

PCT Pub. Date: Apr. 30, 1992

[30] Foreign Application Priority Data

Oct. 19, 1990 [DE] Germany ............... 40 33 343.4

[51] Int. Cl.⁶ ............... A61L 25/00; C08F 20/10
[52] U.S. Cl. ............... 523/116; 523/117; 523/118; 523/218; 604/56; 604/82; 606/92
[58] Field of Search ............... 523/116, 117, 523/118; 604/56, 82; 606/92

[56] References Cited

U.S. PATENT DOCUMENTS

| | | | |
|---|---|---|---|
| 4,927,866 | 5/1990 | Purrmann et al. | 523/116 |
| 5,236,971 | 8/1993 | Murray | 523/116 |

FOREIGN PATENT DOCUMENTS

| | | |
|---|---|---|
| 0369034 | 5/1990 | European Pat. Off. . |
| 0016906 | 1/1980 | Germany . |
| WO86/01725 | 3/1986 | Germany . |
| 0386525 | 2/1990 | Germany . |
| WO87/04110 | 7/1987 | WIPO . |

*Primary Examiner*—Paul R. Michl
*Assistant Examiner*—Andrew E. C. Merriam
*Attorney, Agent, or Firm*—Kinney & Lange, P.A.

[57] ABSTRACT

The invention relates to a material in the form of a three-dimensional conglomerate of polymer particles which is used as a starting material for the preparation of bone cement. The conglomerate is a solid with a uniform pore system and is prepared by bonding the polymer particles to one another at their points of contact or connecting them at their surfaces. After addition of the monomer the material is prepared to a self-curing bone cement and mixed.

32 Claims, 1 Drawing Sheet

MATERIAL AS A STARTING MATERIAL FOR THE PREPARATION OF BONE CEMENT, PROCESS FOR ITS PREPARATION AND PROCESS FOR THE PREPARATION OF BONE CEMENT

BACKGROUND OF THE INVENTION

The invention relates to a material as a starting material for the preparation of bone cement, a process for its preparation and a process for the preparation of bone cement.

In the surgery and orthopaedics of the locomotor system the replacement of a joint by an artificial joint has become a routine operation. The most common method here is to anchor metal prosthetic components in bone by means of a plastic mass which is also known as bone cement. The known bone cements are cold polymerizing two-component based plastics consisting of a monomer and a powdery polymer component in the form of spheres or granules. All the normal commercial bone cements are prepared with a polymethylmethacrylate (PMMA) base. Attempts to mix the two components of these bone cements have shown that homogeneity on the one hand and avoidance of bubbles on the other hand are the main problems in the mixing techniques of such two-component plastics. This is particularly the case when antibiotics are added, which is often difficult. In addition, the powder can create dust when shaken during the mixing process and contaminates the air. The powder can invade the respiratory system and indeed as far as the main bronchus, as experimental tests have shown. Furthermore, should mixing be performed under vacuum, the polymer powder is sucked up by the vacuum pump. The powder component is thus the essential obstacle for the preparation of the bone cement within a closed system which, on the other hand, would certinaly be welcomed from an industrial medicine point of view. Tests to evacuate the powder are incomplete to date in so far as it has not been possible in this way to guarantee a sufficient polymer sphere inclusion in the matrix of the bone cement. The incorporation of any filler particles, such as radiographic contrast agents or osteoinductive substances, presents even greater problems.

The object underlying the present invention is thus to overcome the above problems and to simplify the handling of the polymer powder during preparation of bone cement.

SUMMARY OF THE INVENTION

The invention is based on the idea of converting the powdery polymer component, the particles of which are usually in spherical form, into a solid in the form of a conglomerate before the mixing process. The polymer component of the bone cement is solidified similarly to cube sugar. The porosity of this conglomerate can be controllably adjusted and standardized and the polymer can be solidified such that evacuation is possible. Different porosities can be obtained by varying the size of the polymer particles, the bulk density and the nature of connection of the particles. According to the invention the polymer component of the bone cement is thus a porous pressed part of densely packed polymers connected to one another preferably at their points of contact, between which a pore system is formed.

With the present invention it is possible to create conditions which reproducibly guarantee a homogeneous mixture in the preparation of the bone cement, and indeed irrespective of the skill or ability of the person preparing the mixture. A stabilized polymer bond according to the invention is also to be safely evacuated and indeed before packing but also after the bone cement has been mixed or prepared.

The bone cement's polymer component solidified according to the present invention can be handled easily and safely like a cartridge.

Radiographs in a scanning electronic microscope show that according to the invention there is sufficient space between the polymer particles for a stable polymer/matrix bond. Thus, the conditions are created for a closed system in the preparation and possibly the application of the bone cement by orthopaedics.

The solidified polymer component can be subjected to a preevacuation in a simple manner. The mixing tests with the polymer cartridges according to the invention show that once the monomer is added it is very rapidly absorbed into the given capillary spaces between the polymer particles connected to one another. The components are preferably mixed under vacuum using a mixer which is coated with teflon® or another suitable material, to which the bone cement does not adhere. It has also been shown that the distribution of the polymer powder according to the invention is considerably more uniform than when the powder is poured directly into the monomer liquid without producing a powder conglomerate, and in particular when compared to bone cements wherein initially the powder is provided and the monomer is poured onto the powder heap.

The polymer conglomerate can be welded into a film or membrane of PMMA in order to seal it. The PMMA is solubilized when immersed into the monomer and the monomer is absorbed into the cavity system of the conglomerate.

Advantageously, the conglomerate of the polymer particles can be pressed into the form of a circular cylinder, for example into tablet form. The press mold can be specially designed so that one or several canals, for example a canal system, are formed in the tablet, via which the monomer when added can reach all the polymer particles within the tablet as quickly as possible and virtually simultaneously. For example, several canals arranged concentrically and extending in the axial direction of the tablet cylinder can be provided in the tablet. However, any other canal system which guarantees that the monomer comes into contact with all the polymer particles as quickly as possible during mixing is also possible.

According to the invention all normal bone cement polymer components can be used. Particularly preferred are acrylate or polyacrylate based polymers, a copolymer of an acrylate and methacrylate or a mixture thereof.

According to the invention it is particularly easy to additionally incorporate filler particles into the polymer component present in the form of a conglomerate, for example radiographic contrast agents or bone-inducing particles, in a homogeneous distribution. The filler particles can be in the form of spheres, granules or threads. Preferred sizes of the spheres are between 5 and 300 µm, especially preferred 50 to 300 µm, and the threads between 0.5 and 5 mm, preferably not greater than 3.5 mm.

The material according to the present invention and serving as a starting material for the preparation of bone cement can be prepared in various ways. It is important that the polymer particles are connected to one another to form a porous solid which is also stable during evacuation. For example, the polymer particles can be bonded to one another at their points of contact by means of heat. For this, temperatures between 70° and 120° C. are usually necessary, depending on the starting material used. The polymer particles can also be connected to one another at their surfaces by pressurization. Furthermore, a pressed part can be prepared and solidified by applying heat and pressure simultaneously. In this case, preferred pressures lie between 1 and 10 bar, preferably at about 5 bar.

It is also possible to prepare the conglomerate by chemical treatment, wherein the polymer particles or granules are preferably placed into a mold and a solvent, such as acetone vapor, is passed through, preferably during simultaneous evacuation.

The material according to the present invention in the form of a conglomerate or a cartridge of polymer particles bonded to one another or compressed by pressure has a further advantage in medical techniques. PMMA materials, which are admitted as bone cements, have recently been increasingly used in injection molding processes. In order to produce biocompatible implant parts it is necessary to prepare granules from the powder material which pass through the worms in the drawing engines of the injection molding machines better and more reproducibly than powder. These granules were previously prepared by grinding cured bone cements. According to the invention it is now possible to feed the solidified polymer cartridges or conglomerates as a whole into the machine where they are granulated. Furthermore, it is also possible to process the polymer cartridges or conglomerates in a simple manner initially in a granulating machine to granules which are suitable for injection molding machines. Here it is advantageous to bond the polymer particles particularly tightly when preparing the material or the conglomerate, using higher temperatures of preferably 120° to 180° C., more preferably about 150° C., optionally with simultaneous pressurization.

BRIEF DESCRIPTION OF THE DRAWINGS

The invention is described in more detail below by means of the figure and the examples.

The FIGURE shows the parts of a press mold in detached state for the preparation of the material according to the invention in the form of a pressed part which is used as a starting material for the preparation of bone cement.

DETAILED DESCRIPTION OF THE PREFERRED EMBODIMENTS

Example 1

Figure 1:
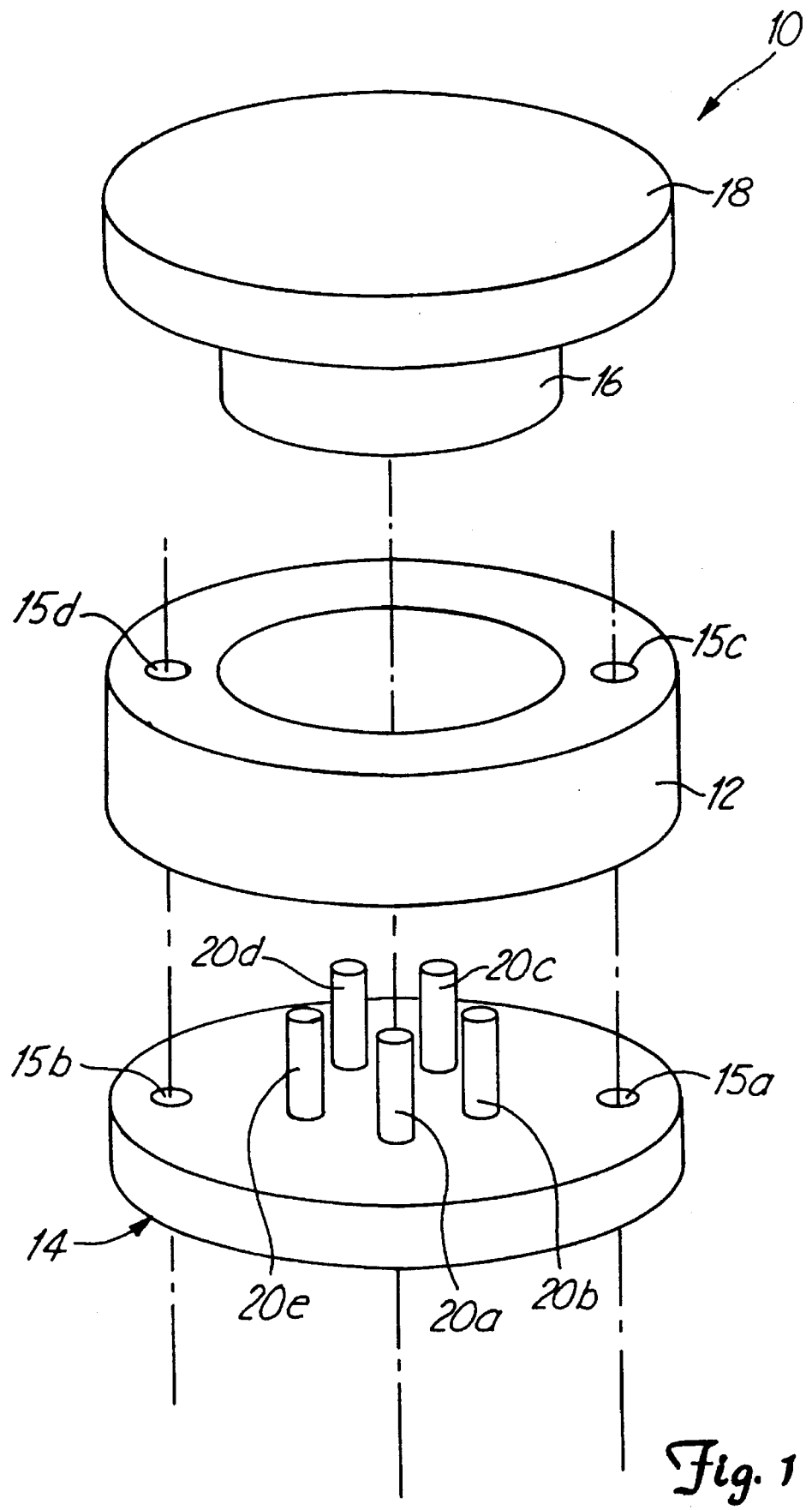

According to FIG. 1 a cylinder 10, preferably of steel, is provided as a pressed part, comprising a hollow cylindrical body 12 and a detachable base 14. The body 12 and the base 14 can, for example, be connected by means of screws (not shown) which are driven through bore holes 15a to 15d. Furthermore, the pressed part has a cylindrical piston 16 and a lid 18 as an integral part of the piston. The outer diameter of the piston 16 essentially corresponds to the inner diameter of the hollow cylindrical body 12 and the piston 16 can be tightly inserted into the body 12. In a preferred embodiment the cylindrical body 12 of the pressed part has a outer diameter of 90 mm, an inner diameter of 55 mm and a height of 20 mm. On the base 14 of the pressed part five cylindrical pins 20a to 20e are arranged concentrically in a radius of 15 mm from the centre of the base. In a preferred embodiment the pins are 15 mm high and have a diameter of 6 mm.

In order to prepare the material according to the invention in the form of a pressed part the two parts 12 and 14 of the pressed part are firstly connected to one another. 40 g of the polymer component of a normal bone cement in the form of a bead or sphere polymer, to which 6 g of zirconium dioxide are added as a radiographic contrast agent, are then poured in and allowed to settle by means of a vibrator. The piston 16 is then inserted into the hollow cylindrical body 12 and placed onto the bone cement bead polymer. The lid 18 of the piston 16 is loaded with a force of about 100N and the pressed part is left for 30 minutes in a dry box at 105° C. After the pressed part is detached the conglomerate prepared in this manner can be taken from the originally powdery polymer particles of the pressed part as a solid tablet. After adding dibenzoyl peroxide, which serves as a polymerization catalyst in the preparation of the bone cement, the conglomerate in the form of a tablet is packed in a suitable tablet tube and prepared for gas sterilization by means of ethylene oxide.

Example 2

The polymer particle conglomerate prepared according to Example 1 is evacuated after gas sterilization in a sterile packing unit and vacuum welded in a tablet tube. The dimensions of the conglomerate in the form of a tablet and of the tablet tube are selected such that they are adapted to a mixing system which is used for preparing the bone cement by mixing with a suitable monomer. Such a mixing system is described, for example, in EP-A-261182.

Although the present invention has been described with reference to preferred embodiments workers skilled in the art will recognize that changes may be made in form and detail without departing from the spirit and scope of the invention.

What is claimed is:

1. A bone cement polymer component as a starting material for preparing bone cement, wherein the polymer component comprises a three-dimensional conglomerate of polymer particles and wherein the polymer component is a solid and contains a pore system.

2. The bone cement polymer component according to claim 1, wherein the pore system is uniform.

3. The bone cement polymer component according to claim 1, wherein the polymer particles are selected from the group consisting of prepolymers of polyacrylates or polymethacrylates, a copolymer of an acrylate and a methacrylate and mixtures thereof.

4. The bone cement polymer component according to claim 1, wherein the conglomerate is packed or welded in evacuated state.

5. The bone cement polymer component according to claim 4, wherein the conglomerate is evacuated in a vessel.

6. The bone cement polymer component according to claim 1, wherein the conglomerate additionally contains filler particles in a form selected from the group consisting of spheres, granules and threads.

7. The bone cement polymer component according to claim 6, wherein the filler particles are radiographic contrast agents or bone-inducing particles.

8. The bone cement polymer component according to claim 6, wherein the filler particles are between 50 and 300 µm in size.

9. The bone cement polymer component according to claim 1, wherein the polymer particles are pressed into a conglomerate in tablet form.

10. The bone cement polymer component according to claim 1, wherein cavities in the form of a canal system are provided in the conglomerate.

11. The bone cement polymer component according to claim 1, wherein the polymer particles in the conglomerate are bonded to one another at their points of contact.

12. A process for preparing a bone cement polymer component comprising:

providing powdered polymer particles: and heating the powdered polymer particles at temperatures between 70° and 120° C. such the polymer particles are bonded to one another at their points of contact and converted into a three-dimensional conglomerate of polymer particles wherein the conglomerate is a solid and contains a pore system.

13. A process for preparing a bone cement polymer component comprising:

providing powdered polymer particles; and pressurizing the polymer particles such that the polymer particles are connected to one another at their surfaces and converted into a three-dimensional conglomerate of polymer particles wherein the conglomerate is a solid and contains a pore system.

14. A process for preparing a bone cement polymer component comprising:

providing powdered polymer particles; and applying heat between 50° and 150° C.: applying simultaneously with the heat pressurization between 1 and 10 bar, such that the powdered polymer particles are solidified into a three-dimensional solid conglomerate having a pore system.

15. A process for preparing a bone cement polymer component comprising:

providing powdered polymer particles; and chemically treating the polymer particles to form a solid in the form of a three-dimensional, solid conglomerate of polymer particles containing a pore system.

16. The process according to claim 15, wherein a solvent is passed through the powder of the polymer particles under vacuum, whereby the polymer particles adhere to one another and form the conglomerate.

17. The process according to claim 16, wherein acetone vapors are used as the solvent.

18. The process according to claim 13, wherein a press mold is used for pressurization which is designed such that a canal system is provided in the formed conglomerate.

19. The process according to claim 18, wherein the press mold is cylindrical and comprises several means in its interior which serve as space retainers for the canal system.

20. The bone cement polymer component according to claim 1, wherein the polymer component is prepared and mixed into a self-curing bone cement by adding a monomer.

21. A process for preparing bone cement comprising:

converting polymer particles into a conglomerate in the form of a solid comprising a pore system; and adding a monomer to the conglomerate.

22. The bone cement polymer component according to claim 4, wherein the conglomerate is welded under vacuum pressure.

23. The bone cement polymer component according to claim 4, wherein the conglomerate is welded under vacuum pressure within a packing material, said, packing material being made of an airtight PMMA film.

24. The bone cement polymer component according to claim 6, wherein the filler particles have a thread length between 0.5 and 5 mm.

25. The bone cement polymer component according to claim 6, wherein the filler particles have a thread length up to 3.5 mm.

26. The bone cement polymer component according to claim 1, wherein the polymer particles in the conglomerate are connected to one another at their surfaces.

27. The process according to claim 14, wherein the heat is applied between 70° and 100° C.

28. The process according to claim 14, wherein the pressure is applied at between 3 to 5 bar.

29. The process according to claim 14, wherein the pressure is applied at approximately 5 bar.

30. The process according to claim 18, wherein the means which serve as spore retainers for the canal system includes pins.

31. The process of claim 21 further comprising the step of mixing the monomer with the conglomerate.

32. Bone cement made according to the process of claim 21.

* * * * *